(12) United States Patent
Hartfelder et al.

(10) Patent No.: US 9,687,300 B2
(45) Date of Patent: Jun. 27, 2017

(54) WIRE MANAGEMENT FEATURED INTEGRATED INTO PETG TRAY FOR EM TRACKABLE DISPOSABLE PRODUCTS

(71) Applicant: Medtronic Xomed, Inc., Jacksonville, FL (US)

(72) Inventors: Teresa Hartfelder, Yulee, FL (US); James M. Inabinett, Saint Johns, FL (US)

(73) Assignee: MEDTRONIC XOMED, INC., Jacksonville, FL (US)

( * ) Notice: Subject to any disclaimer, the term of this patent is extended or adjusted under 35 U.S.C. 154(b) by 3 days.

(21) Appl. No.: 14/327,215

(22) Filed: Jul. 9, 2014

(65) Prior Publication Data
US 2015/0114864 A1 Apr. 30, 2015

Related U.S. Application Data

(60) Provisional application No. 61/898,229, filed on Oct. 31, 2013.

(51) Int. Cl.
| | |
|---|---|
| *B65D 83/10* | (2006.01) |
| *A61B 19/02* | (2006.01) |
| *B65B 69/00* | (2006.01) |
| *A61B 50/00* | (2016.01) |
| *A61B 50/33* | (2016.01) |
| *A61B 50/30* | (2016.01) |
| *A61B 34/20* | (2016.01) |

(52) U.S. Cl.
CPC .......... *A61B 19/0271* (2013.01); *A61B 50/00* (2016.02); *A61B 50/33* (2016.02); *B65B 69/00* (2013.01); *A61B 2034/2051* (2016.02); *A61B 2050/005* (2016.02); *A61B 2050/314* (2016.02)

(58) Field of Classification Search
CPC .......... A61B 19/0271; A61B 2050/314; A61B 2019/0279; A61B 2017/00637; A61B 2046/234; A61B 2050/3015; B65B 69/00; B25H 3/06
USPC .............. 206/370, 63.5, 570, 438, 564, 207; 53/549; 606/47
See application file for complete search history.

(56) References Cited

U.S. PATENT DOCUMENTS

| | | |
|---|---|---|
| 5,098,391 A | 3/1992 | Pantages et al. |
| 5,099,994 A | 3/1992 | Kalinski et al. |

(Continued)

FOREIGN PATENT DOCUMENTS

WO WO-2015066288 A1 5/2015

OTHER PUBLICATIONS

International Search Report and Written Opinion mailed Mar. 15, 2015 for PCT/US2014/063092 claiming priority to U.S. Appl. No. 14/327,215.

(Continued)

*Primary Examiner* — Anthony Stashick
*Assistant Examiner* — James M Van Buskirk
(74) *Attorney, Agent, or Firm* — Harness Dickey

(57) ABSTRACT

A packaging assembly for an electromagnetic trackable surgical tool and wiring thereof. The packaging assembly includes a first tray with at least one first retention member configured to couple the surgical tool to the first tray. The packaging assembly further includes a second tray configured to couple with the first tray. The second tray has at least one second retention member configured to couple the wiring of the surgical tool to the second tray.

19 Claims, 8 Drawing Sheets

(56) References Cited

U.S. PATENT DOCUMENTS

| | | | |
|---|---|---|---|
| 5,779,053 | A | 7/1998 | Partika et al. |
| 8,504,139 | B2 | 8/2013 | Jacobsen et al. |
| 2006/0086634 | A1 | 4/2006 | Steppe |
| 2007/0041864 | A1* | 2/2007 | Forsyth ..................... A61L 2/04 422/1 |
| 2013/0256167 | A1* | 10/2013 | Scott ........................ A61L 2/26 206/370 |

OTHER PUBLICATIONS

Invitation to Pay Additional Fees and, where applicable, Protest Fee mailed Jan. 28, 2015 for PCT/US2014/063092 claiming priority to U.S. Appl. No. 14/327,215.

Australian Office Action dated Aug. 30, 2016 for Australian Application No. 2014342252 which claims benefit of PCT/US2014/063092 filed Oct. 31, 2013.

Canadian Office Action dated Mar. 8, 2017 for Canadian Application No. 2,929,236 which claims benefit of PCT/US2014/063092 which claims benefit of U.S. Appl. No. 14/327,215, filed Jul. 9, 2014.

* cited by examiner

WIRE MANAGEMENT FEATURED INTEGRATED INTO PETG TRAY FOR EM TRACKABLE DISPOSABLE PRODUCTS

CROSS-REFERENCE TO RELATED APPLICATION

This application claims the benefit of U.S. Provisional Patent Application No. 61/898,229 filed on Oct. 31, 2013, the disclosure of which is incorporated herein by reference.

FIELD

The present disclosure relates to a wire management feature integrated into packaging for an electromagnetic (EM) trackable tool.

BACKGROUND

This section provides background information related to the present disclosure, which is not necessarily prior art.

Electromagnetic trackable tools can be used in a variety of surgical procedures. Such tools are typically packaged in a manner that will maintain the sterility of the tools as they are transported into a sterile surgical field. While existing packaging is suitable for its intended use, it is subject to improvement. For example, a wire management feature integrated into the packaging to manage wiring of the tools would be desirable.

SUMMARY

This section provides a general summary of the disclosure, and is not a comprehensive disclosure of its full scope or all of its features.

The present teachings provide for a packaging assembly for an electromagnetic trackable surgical tool and wiring thereof. The packaging assembly includes a first tray with at least one first retention member configured to couple the surgical tool to the first tray. The packaging assembly further includes a second tray configured to couple with the first tray. The second tray has at least one second retention member configured to couple the wiring of the surgical tool to the second tray.

The present teachings also provide for a packaging assembly for an electromagnetic trackable surgical tool and wiring thereof. The packaging assembly includes a first tray with the electromagnetic trackable surgical tool coupled to the first tray. A second tray is coupled to the first tray such that the electromagnetic trackable surgical tool is between the first tray and the second tray. The wiring of the electromagnetic trackable surgical tool is coupled to the second tray. A connector of the wiring is coupled to the second tray. Sterilly sealed within a flexible container is the first tray with the electromagnetic trackable surgical tool coupled to the first tray, and the second tray coupled to the first tray. The wiring and the connector are coupled to the second tray.

The present teachings further provide for a method for introducing a sterile electromagnetic trackable surgical tool and wiring thereof into a sterile environment. The method includes opening a flexible container and passing contents of the flexible container into the sterile environment. The contents include the following: a first tray; the electromagnetic trackable surgical tool coupled to the first tray; a second tray coupled to the first tray such that the electromagnetic trackable surgical tool is between the first tray and the second tray; the wiring coupled to the second tray; and a connector of the wiring coupled to the second tray. The method further includes the following: passing the contents of the flexible container into the sterile environment; decoupling the connector from the second tray; connecting the connector to equipment within the sterile environment; decoupling the wire from the second tray and arranging the wire within the sterile environment; decoupling the first tray and the second tray to permit access to the electromagnetic trackable surgical tool; and decoupling the electromagnetic trackable surgical tool from the first tray.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
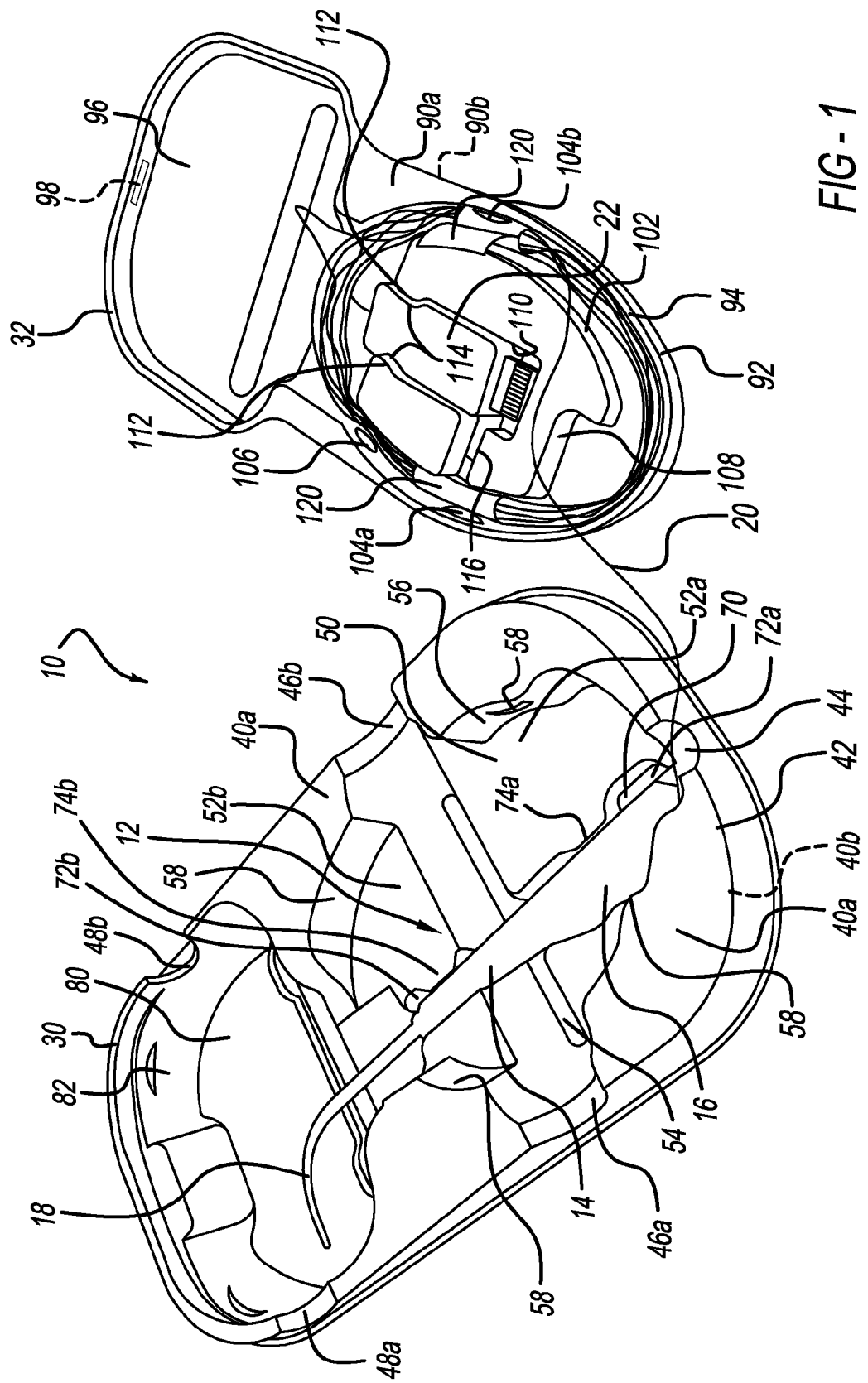
FIG. 1 is a perspective view of a packaging assembly according to the present teachings illustrating a first tray separated from a second tray, an electromagnetic trackable tool and wiring thereof is mounted to the packaging assembly.
Figure 2:
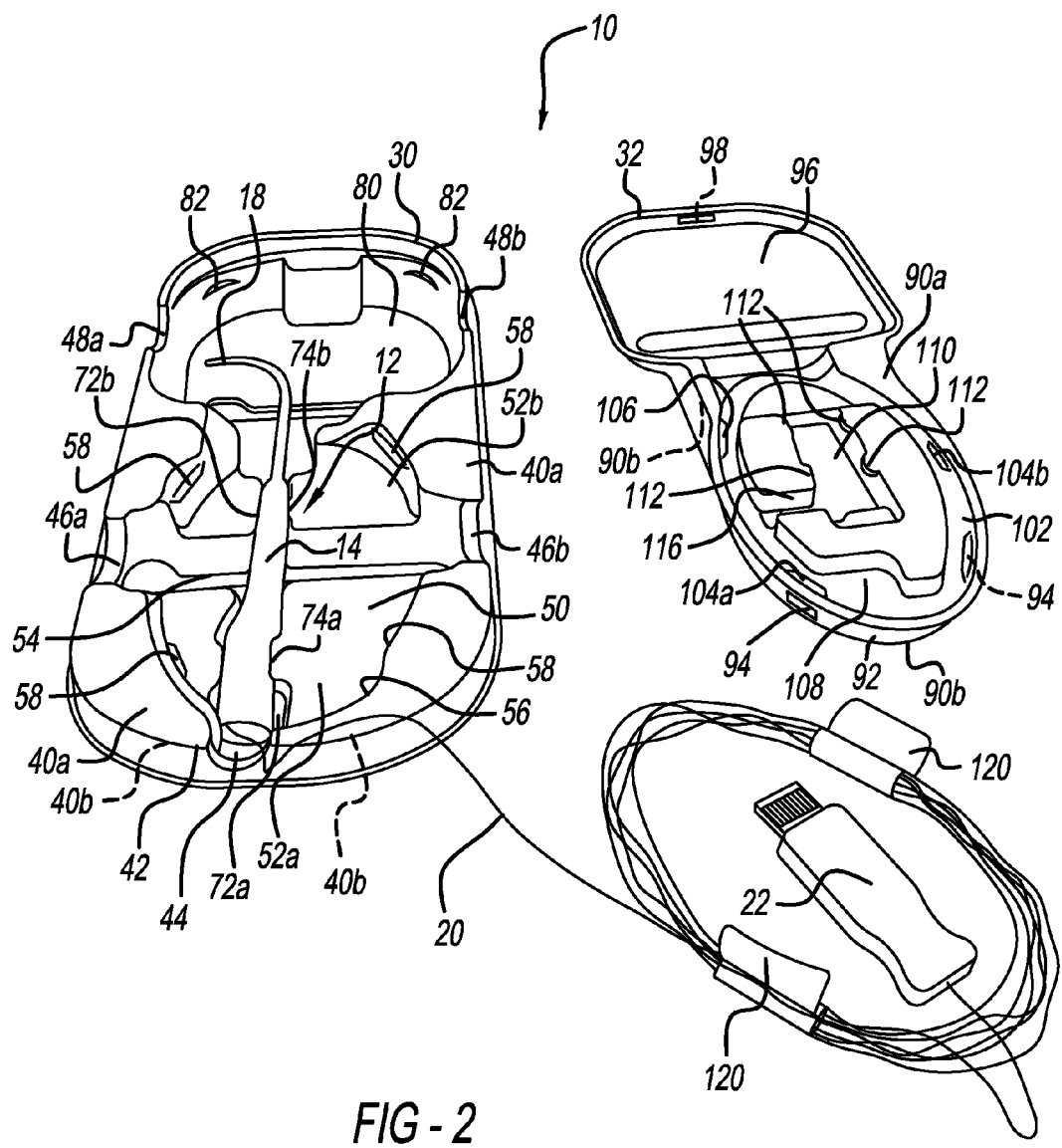
FIG. 2 is another perspective view of the packaging assembly of FIG. 1 illustrating the first tray separated from the second tray.

With initial reference to FIGS. 1 and 2, a surgical packaging assembly according to the present teachings is generally illustrated at reference numeral 10. The surgical packaging assembly 10 is configured for packaging a tool assembly 12, such as an electromagnetic trackable surgical tool assembly. The tool assembly 12 generally includes a handle 14, an electromagnetic tracker 16, and a probe 18 extending from the handle 14. A wire 20 is coupled to the electromagnetic tracker 16 and extends from the electromagnetic tracker 16 and the handle 14 to a connector 22. Though the surgical packaging assembly 10 of the present application is described as being configured to house the tool assembly 12, the surgical packaging assembly 10 can be configured to house any suitable surgical tool including a wiring assembly.

The electromagnetic tracker 16 can be any suitable tracking device, such as a coil array, for tracking location of the tool assembly 12, and particularly the probe 18, within an electromagnetic image guided surgical system. The probe 18 can be removably coupled to the handle 14. In place of the probe 18, any suitable surgical tool can be coupled to the handle 14, such as a cutting blade.

The tool assembly 12 can be used in any suitable electromagnetic image guided surgical system, such as the surgical system described in U.S. Pat. No. 8,504,139 at reference numeral 10 of FIG. 1 thereof. U.S. Pat. No. 8,504,139 ("'139 patent") issued on Aug. 6, 2013 to Medtronic Xomed, Inc., and is incorporated herein by reference. The surgery system 10 of the '139 patent includes a coil array container 68 with a navigation hand piece interface 70, to which connector 22 of the tool assembly 12 of the present application may be coupled to. The location of the tool assembly 12 within the surgery system 10 of the '139 patent can be tracked using the work station 36 of the '139 patent.

The packaging assembly 10 generally includes a first or bottom tray 30 and a second or top tray 32. The bottom tray 30 and the top tray 32 can be made of any suitable material, such as polyethylene terephthalate glycol, or any other suitable polymer. Each of the bottom and top trays 30 and 32 can be unitary or monolithic, and manufactured in any suitable manner, such as by injection molding, flow molding, or vacuum forming.

The bottom or first tray 30 generally includes a first interior surface or first upper surface 40a and a first exterior surface or first lower surface 40b opposite thereto. At an outer edge 42 of the upper surface 40a is defined an end recess 44, a first pair of side recesses 46a and 46b, and a second pair of side recesses 48a and 48b. The end recess 44 can be configured to accommodate passage of the wire 20 therethrough, for example. The first and second pairs of side recesses 46a, 46b, 48a, and 48b can be configured to provide openings through which the top tray 32 can be grasped to facilitate separation of the top tray 32 from the bottom tray 30 when the bottom and top trays 30 and 32 are coupled together, as described herein.

Recessed beneath the upper surface 40a is a first recess 50, which includes a first portion 52a and a second portion 52b separated by a trough 54, which is recessed beneath the first and second portions 52a and 52b. Extending between the upper surface 40a and the first recess 50 is a wall 56, which extends generally perpendicular to the first recess 50. Protruding from the wall 56 are a plurality of first tray retention members or tabs 58, which as described herein are configured to cooperate with the top tray 32 to secure the top tray 32 to the bottom tray 30 and to secure at least a portion of the top tray 32 within the first recess 50. Any suitable member of tabs 58 can be included, and the tabs 58 can be located at any suitable position about the wall 56.

Within the first recess 50 is a second recess 70. The second recess 70 includes a first portion 72a recessed within the first portion 52a of the first recess 50, and a second portion 72b recessed within the second portion 52b of the first recess 50. The second recess or tool retention member or tool receptacle 70 is configured to receive at least a portion of the handle 14 and the electromagnetic tracker 16 therein. The second recess 70 includes a first pair of tabs 74a at the first portion 72a, and a second pair of tabs 74b at the second portion 72b. The tabs or tool retention members 74a and 74b are configured to retain the handle 14 and the electromagnetic tracker 16 within the second recess 70.

The bottom tray 30 further defines a third recess 80 into which the probe 18 extends when the handle 14 is seated in the second recess 70. Extending into the third recess 80 from a periphery thereof are one or more tabs or first tray retention members 82. The tabs 82 are configured to cooperate with the top tray 32 in order to couple the bottom and top trays 30 and 32 together and retain a portion of the top tray 32 within the third recess 80, as further described herein.

The top or second tray 32 generally includes a second exterior surface or second upper surface 90a and a second interior surface or second lower surface 90b opposite thereto. Extending between the upper surface 90a and the lower surface 90b is a wall 92. The wall 92 defines a plurality of recesses or second tray retention members 94 therein, which are sized, shaped, and arranged to cooperate with the tabs 58 of the bottom tray 30 to secure the bottom and top trays 30 and 32 together, and a portion of the top tray 32 including the wall 92 within the first recess 50 of the bottom tray 30. The top tray 32 further includes a base or handle member 96 defining a plurality of recesses or second tray retention members 98 at an exterior thereof, which are sized, shaped, and arranged in order to cooperate with the tabs 82 of the bottom tray 30 in order to secure the base or handle member 96 within the third recess 80 of the bottom tray 30.

The top tray 32 further defines a generally oval recess or wire receptacle 102, which is recessed beneath the upper surface 90a. The oval recess 102 is generally sized and shaped to accommodate a majority of the wire 20 therein. In order to retain the wire 20 in the recess 102, at least a first wire retention member or tab 104a and a second wire retention member or tab 104b can be included. Each of the first tab 104a and the second tab 104b extend into the recess 94 to generally abut the wire 20 after the wire 20 has been passed over the first and second tabs 104a and 104b in order to prevent the wire 20 from falling out from within the recess 94. Any suitable coupling member, such as adhesive members 120 or tape, can be wrapped around the wire 20 to facilitate retention of the wire 20 within the oval recess 102. The coupling members 120 can be arranged at any suitable position on portions of the wire 20 within the oval recess 102, such as at portions of the wire 20 seated beneath the first and second tabs 104a and 104b.

Additional tabs or wire retention members 106 can also be included to retain the wire 20 within the oval recess 102. The tabs 106 can generally be arranged opposite to the recesses 94, and can be generally the opposite or inverse of the recesses 94. To facilitate removal of the wire 20 out from within the oval recess 102, an enlarged recess area 108 can be included in the oval recess 102, which generally provides a clearance between the wire 20 and the top tray 32 to facilitate grasping of the wire 20.

The top tray 32 can further define a connector receptacle 110, such as generally at a center of the upper surface 90a, which is configured to receive the connector 22 therein. In order to retain the connector 22 within the receptacle 110, one or more connector retention members or tabs 112 can be included, which extend into the receptacle 110. The tabs 112 can be sized, shaped, and arranged to cooperate with various features of the connector 22, such as recesses 114 of the connector 22 in order to retain the connector 22 within the receptacle 110. Extending between the receptacle 110 and the oval recess 102 can be a slot 116, which can provide a clearance to grasp the connector 22 and separate the connector 22 from the top tray 32.

Figure 3:
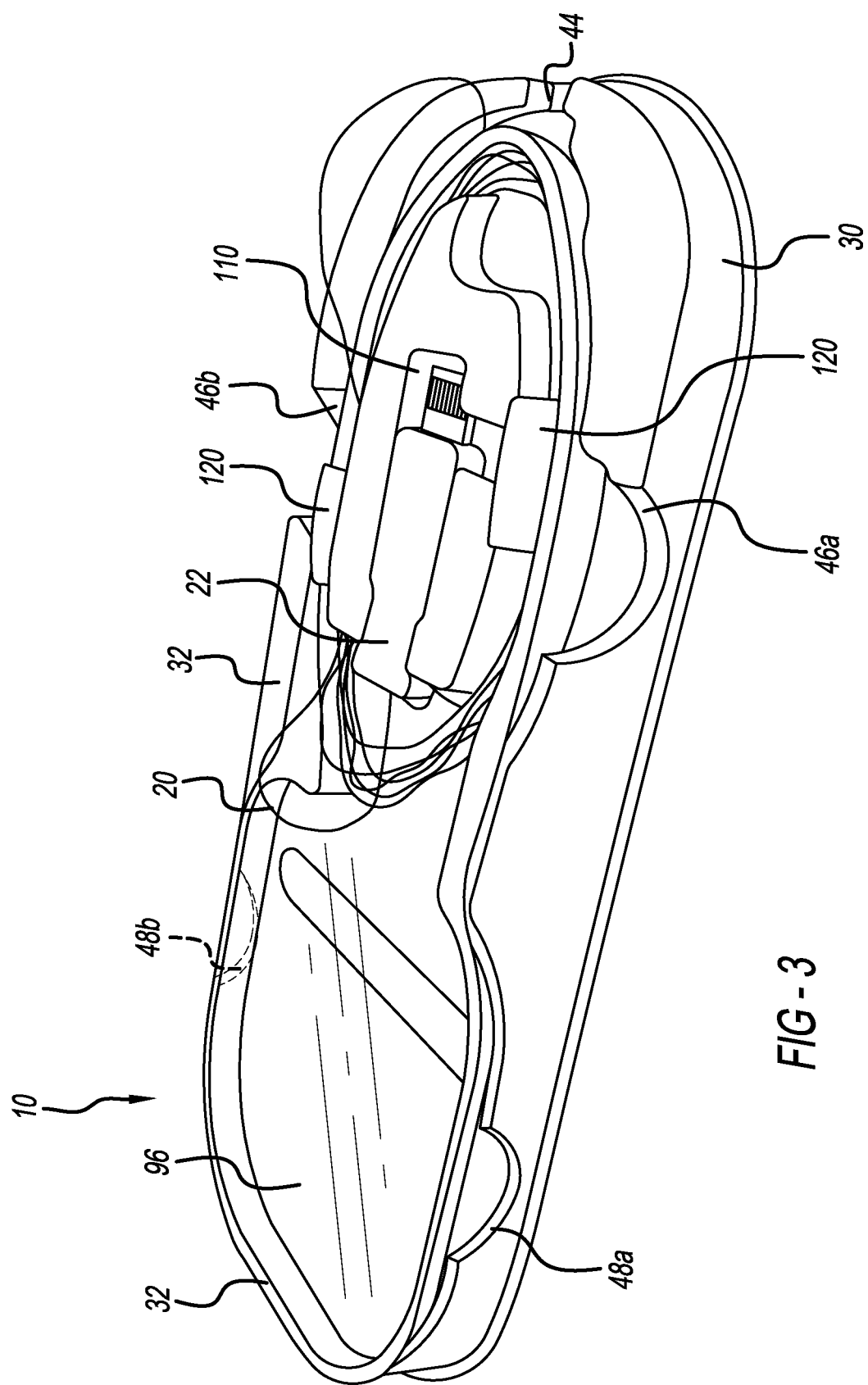
FIG. 3 is a perspective view of the packaging assembly of FIG. 1 illustrating the first tray and the second tray coupled together.
Figure 4:
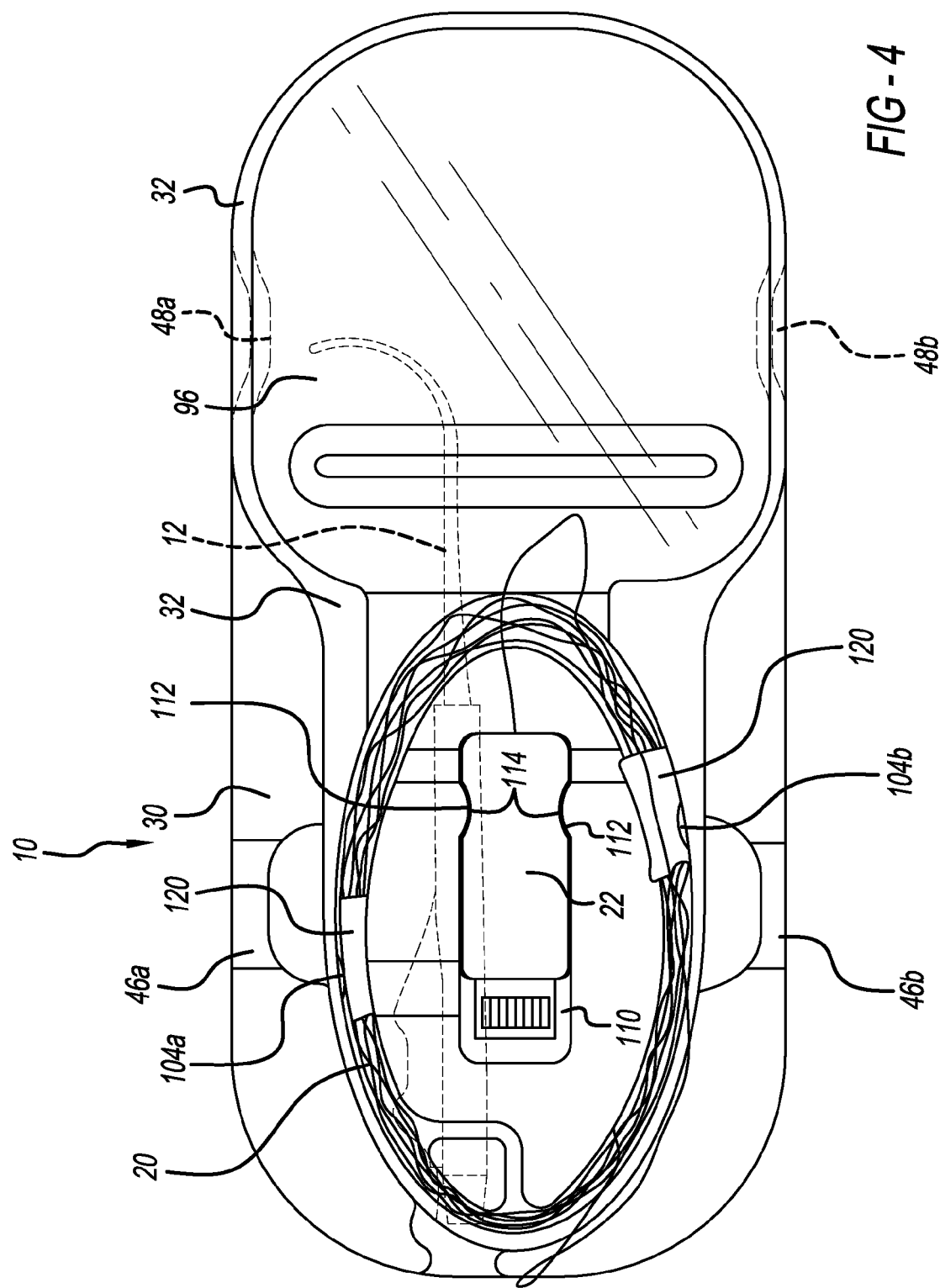
FIG. 4 is planar view of the packaging assembly of FIG. 1 illustrating the first and second trays coupled together.

With additional reference to FIGS. 3 and 4, the packaging assembly 10 with the bottom and top trays 30 and 32 coupled together is shown. The bottom and top trays 30 and 32 are coupled such that the portion of the top tray 32 including the oval recess 102 is generally seated within the first recess 50 of the bottom tray 30. Clearance between the top tray 32 and the bottom tray 30 at the first and second pairs of side recesses 46a, 46b, 48a, and 48b, which facilitate separation of the top tray 32 from the bottom tray 30, can be seen in FIG. 3 for example. The base or handle member 96 of the top tray 32 is generally seated in the third recess 80 of the bottom tray 30. The wire 20 is generally arranged such that it extends from the handle 14 in the electromagnetic tracker 16 through the end recess 44, and up into the oval recess 102 where the wire 20 is wound and secured within the oval recess 102 as described above.

As shown in FIG. 3, for example, the top tray 32 is seated within the bottom tray 30 and only extends minimally therefrom in order to provide the packaging assembly 10 with a minimal profile, which allows the packaging assembly 10 to be fit easily into a sterile barrier system that can be easily sterilized, such as by way of ethylene oxide gas flushing. The majority of the wire 20 is seated within the oval recess 102, and the connector 22 is recessed within the receptacle 110, so as to not add to the profile of the packaging assembly 10.

Figure 5:
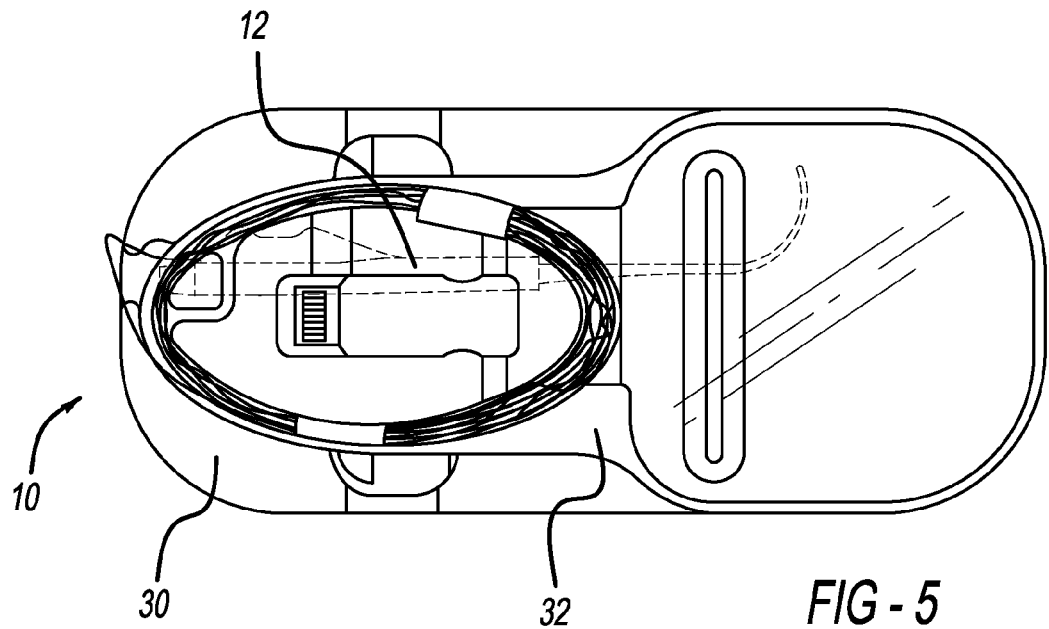
FIG. 5 is a planar view of the packaging assembly of FIG. 1 illustrating the first and second trays coupled together.
Figure 6:
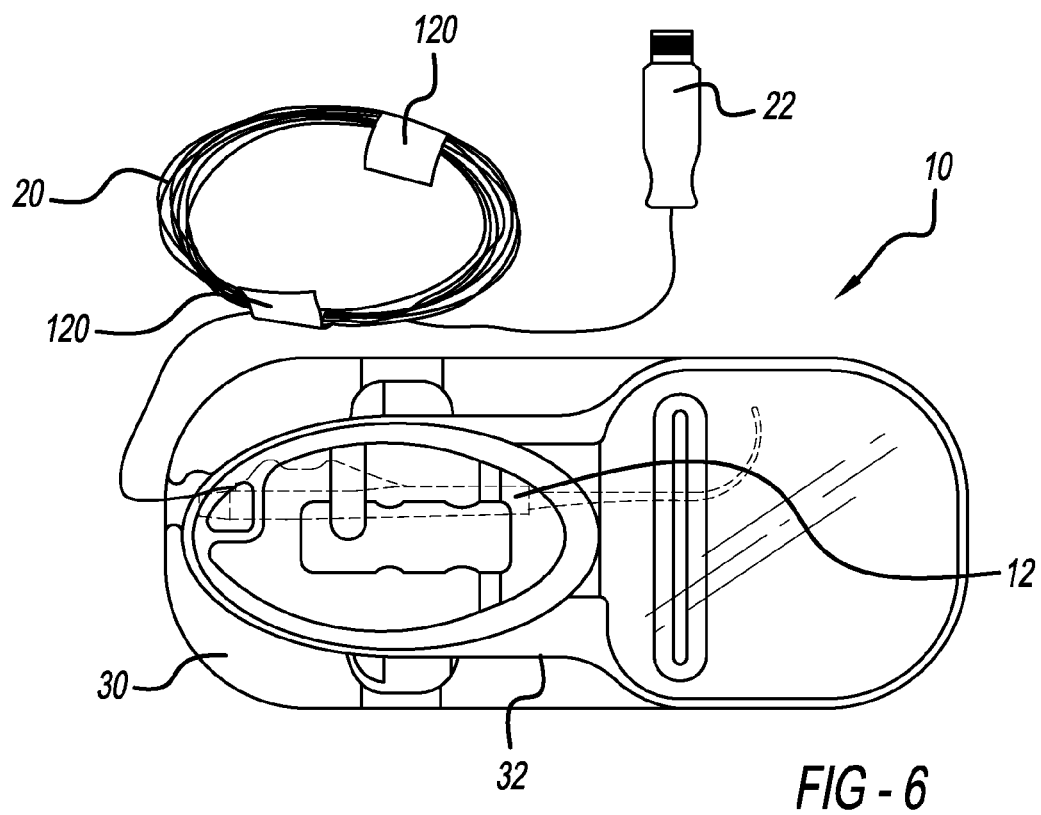
FIG. 6 is a planar view of the packaging assembly of FIG. 1 with the first and the second trays coupled together, the electromagnetic trackable tool coupled to the first tray, and wiring of the electromagnetic trackable tool decoupled from the second tray.
Figure 7:
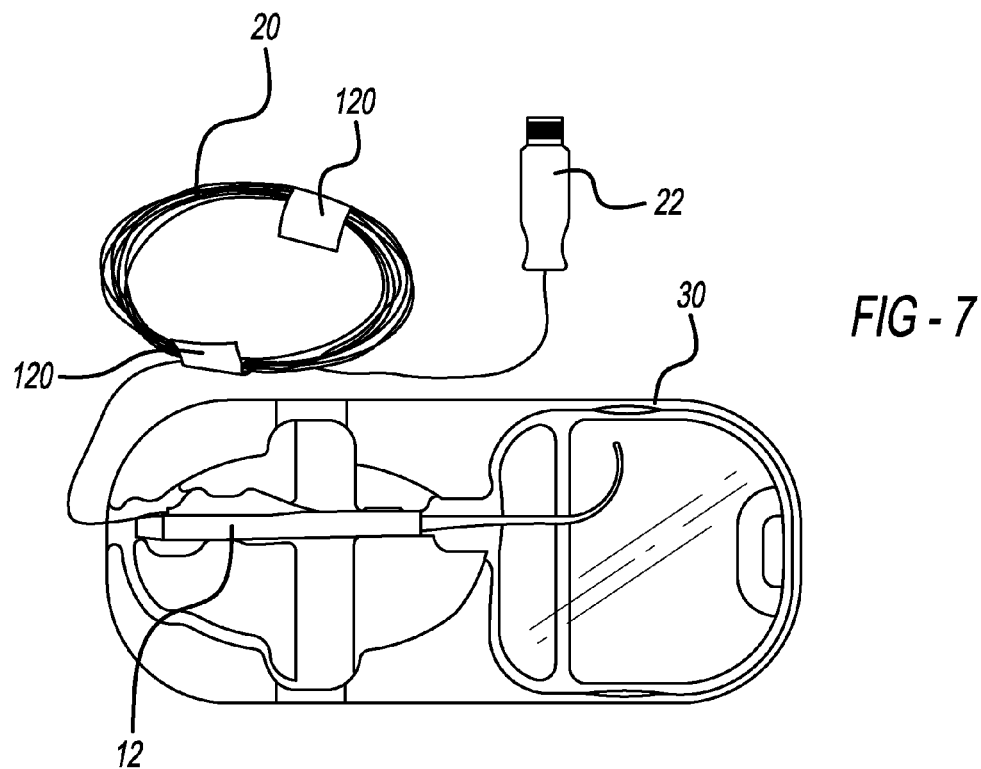
FIG. 7 is a planar view of the first tray illustrating the electromagnetic trackable tool coupled to the first tray and wiring of the electromagnetic trackable tool decoupled from the second tray.
Figure 8:
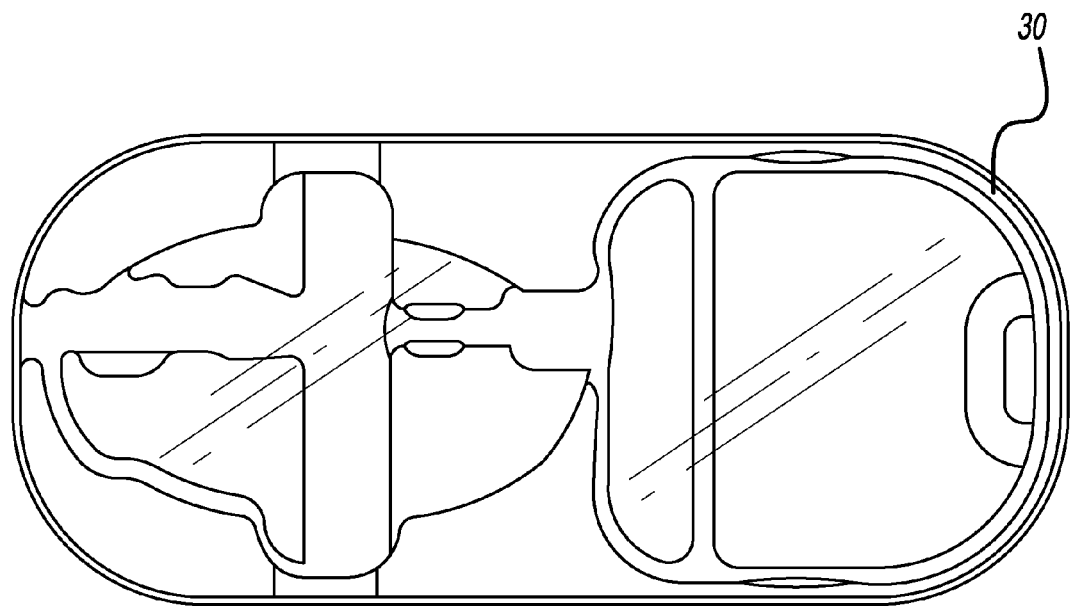
FIG. 8 is a plan view of the first tray.
Figure 9:
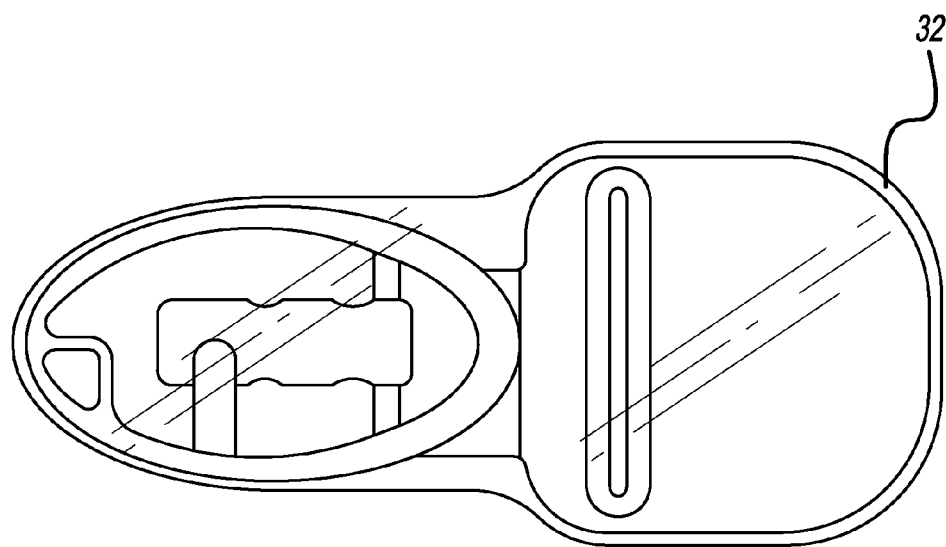
FIG. 9 is a plan view of the second tray.

FIGS. 5-9 illustrate additional views of the packaging assembly 10. FIG. 5 is a top view of the packaging assembly 10 with the top tray 32 coupled to, and generally received within, the bottom tray 30. FIG. 5 is generally similar to FIG. 4. FIG. 6 is similar to FIGS. 4 and 5, but shows the wire 20 pulled out from within the oval recess 102. FIG. 7 illustrates the bottom tray 30 with the top tray 32 removed therefrom. The handle 14 including the electromagnetic tracker 16 and the probe 18 remains coupled to the bottom tray 30 in FIG. 7. FIG. 8 illustrates the bottom tray 30 with the tool assembly 12 completely removed therefrom. FIG. 9 illustrates the top tray 32 independent of the bottom tray 30, and with the wire 20 and connector 22 completely removed therefrom.

Figure 10:
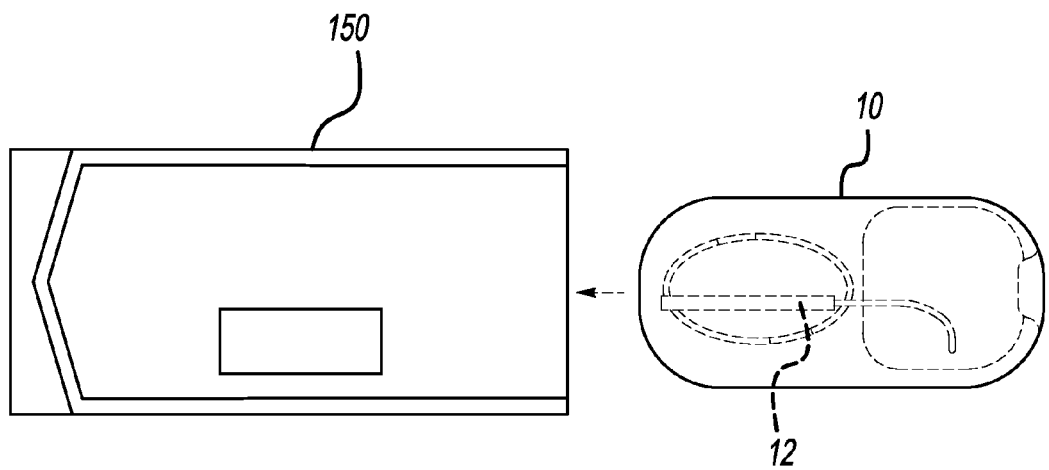
FIG. 10 illustrates additional packaging for the packaging assembly of FIG. 1.
Figure 11:
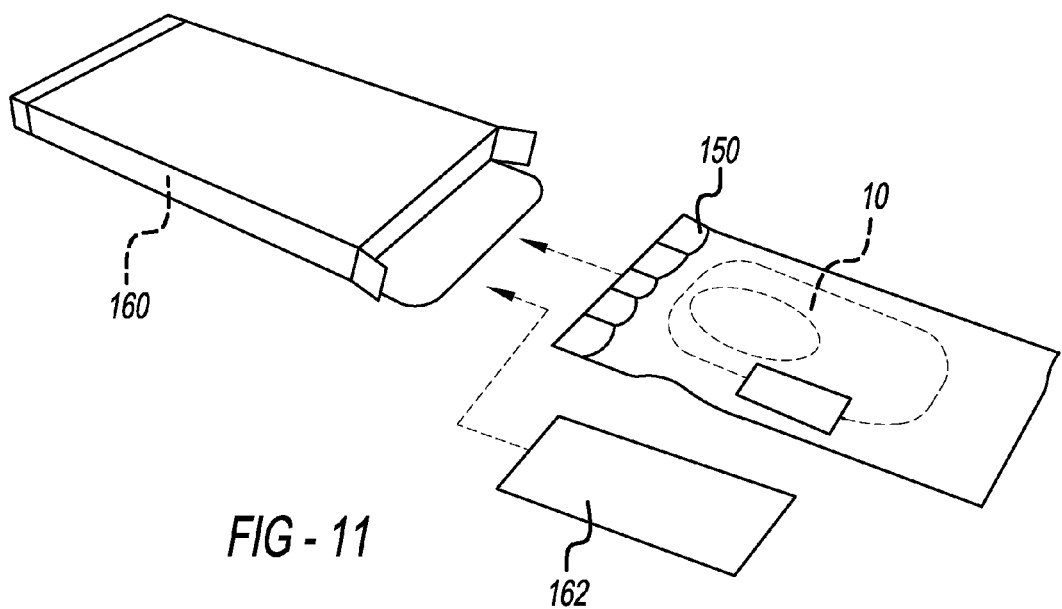
FIG. 11 illustrates yet additional packaging for the packaging assembly of FIG. 1.

With additional reference to FIG. 10, a flexible packaging 150 in which the packaging assembly 10 can be sealed within is illustrated. The flexible packaging 150 can be any packaging suitable to maintain the sterility of the packaging assembly 10 and the tool assembly 12 coupled thereto, and need not be flexible. With additional reference to FIG. 11, a box 160 is illustrated that is configured to receive flexible packaging 150 with the packaging assembly 10 sealed therein, as well as a label 162, which can include information regarding the tool assembly 12.

The packaging assembly 10 thus generally provides a wire management system for the wire 20. Therefore, in use when the flexible packaging 150 is opened and the packaging assembly 10 is passed into the sterile operating field during aseptic presentation (sterile transfer), the wire 20 will be retained in place and coupled to the top tray 32, which will minimize, if not eliminate, any possibility of the wire 20 falling out from within the sterile field or becoming tangled. After the packaging assembly 10 is removed from the flexible packaging 150 and introduced into the sterile field, the connector 22 can be decoupled from the top tray 32 and connected to equipment in the sterile field, such as the navigation hand piece interface 70 set forth in the '139 patent, prior to the top tray 32 being decoupled from the bottom tray 30. The connector 22 can be decoupled in any suitable manner, such as by inserting one's finger or a suitable tool into the slot 116 to pry the connector 22 apart from the top tray 32. With the top tray 32 still coupled to the bottom tray 30, so as to eliminate any need to interact with the handle 14 and the probe 18 and to ensure that the sterility thereof is maintained, the wire 20 can be decoupled from the top tray 32 and arranged about the sterile field as appropriate. The wire 20 can be decoupled from the top tray 32 in any suitable manner, such as by inserting one's finger or a suitable tool into the recess area 108 to pull the wire 20 out from within the oval recess 102.

Once the connector 22 and the wire 20 are positioned as desired, the top tray 32 can be decoupled from the bottom tray 30 in order to gain access to the handle 14 and the probe 18. The top tray 32 can be decoupled in any suitable manner, such as by inserting one's fingers, or a suitable tool, into one or more of the recesses 46a, 46b, 48a, or 48b to pry the top tray 32 apart from the bottom tray 30. The probe 18 will be ready for use without concern of the wire 20 falling from the sterile field or becoming undesirably tangled.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A surgical packaging assembly and system comprising:
   a first tray having a first interior surface and an opposed first exterior surface;
   an electromagnetic trackable surgical tool coupled to the first interior surface of the first tray;
   a second tray having a second interior surface and an opposed second exterior surface and coupled to the first tray such that the electromagnetic trackable surgical tool is between the first interior surface of the first tray and the second interior surface of the second tray;
   a wiring of the electromagnetic trackable surgical tool coupled to the second exterior surface of the second tray; and
   a connector of the wiring coupled to the second exterior surface of the second tray.

2. The surgical packaging assembly and system of claim 1, further comprising:
   the first tray including at least one tool retention member configured to couple the surgical tool to the first tray; and
   the second tray configured to couple with the first tray, the second tray including at least one wire retention member configured to couple the wiring of the tool to the second tray.

3. The surgical packaging assembly and system of claim 2, wherein each of the first tray and the second tray are made of a polymeric material.

4. The surgical packaging assembly and system of claim 3, wherein each of the first tray and the second tray are monolithic.

5. The surgical packaging assembly and system of claim 2, wherein the at least one tool retention member includes a plurality of retention tabs.

6. The surgical packaging assembly and system of claim 5, wherein the retention tabs are integral with the first tray.

7. The surgical packaging assembly and system of claim 2, wherein the at least one wire retention member includes a plurality of retention tabs included with the second tray.

8. The surgical packaging assembly and system of claim 2, wherein the at least one wire retention member includes a recess configured to accommodate the wiring of the surgical tool therein.

9. The surgical packaging assembly and system of claim 8, wherein the at least one wire retention member further includes a plurality of tabs extending partially across the recess and configured to retain the wiring in the recess.

10. The surgical packaging assembly and system of claim 8, wherein the first tray includes a plurality of tray retention members and the second tray includes a plurality of second tray retention members, the first tray retention members and the second tray retention members are configured to cooperate to couple the first tray and the second tray together.

11. The surgical packaging assembly and system of claim 2, wherein the second tray includes at least one connector retention member configured to couple a connector at an end of the wiring to the second tray.

12. The surgical packaging assembly and system of claim 11, wherein the at least one connector retention member is at a receptacle defined within the second tray, the receptacle configured to receive the connector therein.

13. The surgical packaging assembly and system of claim 2, wherein the first tray is configured to receive at least a portion of the second tray therein.

14. The surgical packaging assembly and system of claim 1, wherein each of the first tray and the second tray are both monolithic.

15. The surgical packaging assembly and system of claim 1, wherein the first tray is coupled to the second tray such that the first tray receives at least a portion of the second tray therein.

16. The surgical packaging assembly and system of claim 1, wherein:
the electromagnetic trackable surgical tool is coupled to the first interior surface of the first tray with at least one tool retention member of the first tray;
the wiring is coupled to the second exterior surface of the second tray with at least one wire retention member of the second tray;
the first tray is coupled to the second tray through cooperation between first tray retention members of the first tray and second tray retention members of the second tray; and
the connector is coupled to the second exterior surface of the second tray with at least one connector retention member of the second tray.

17. A method for introducing a sterile electromagnetic trackable surgical tool and wiring thereof into a sterile environment using a packaging assembly comprising:
passing the packaging assembly into the sterile environment, the packaging assembly including:
a first tray;
the electromagnetic trackable surgical tool coupled to the first tray;
a second tray coupled to the first tray such that the electromagnetic trackable surgical tool is between the first tray and the second tray;
the wiring coupled to the second tray; and
a connector of the wiring coupled to the second tray;
before decoupling the first tray from the second tray, decoupling the connector from the second tray;
before decoupling the first tray from the second tray, connecting the connector to equipment within the sterile environment;
before decoupling the first tray from the second tray, decoupling the wire from the second tray and arranging the wire within the sterile environment;
decoupling the first tray from the second tray to permit access to the electromagnetic trackable surgical tool; and
decoupling the electromagnetic trackable surgical tool from the first tray.

18. The method of claim 17, further comprising:
decoupling the electromagnetic trackable surgical tool from at least one tool retention member of the first tray;
decoupling the wiring from at least one wire retention member of the second tray;
decoupling the first tray and the second tray by separating first tray retention members of the first tray from cooperation with second tray retention members of the second tray; and
decoupling the connector from at least one connector retention member of the second tray.

19. A surgical packaging assembly and system comprising:
a packaging assembly having a first tray coupled to a second tray;
a tool receptacle defined within an interior of the coupled first and second trays;
a wire receptacle defined on an exterior surface of the second tray;
a connector receptacle defined on an exterior surface of the second tray;
an electromagnetic trackable surgical tool coupled to the first receptacle;
a wiring of the electromagnetic trackable surgical tool coupled to the second receptacle; and
a connector of the wiring coupled to the third receptacle.

* * * * *